United States Patent
Rapp et al.

(10) Patent No.: US 11,369,522 B2
(45) Date of Patent: *Jun. 28, 2022

(54) PRESSURE-SENSING COMPRESSION BANDAGE

(71) Applicants: Scott Rapp, Mountain View, CA (US); Gary Rapp, Dublin, OH (US)

(72) Inventors: Scott Rapp, Mountain View, CA (US); Gary Rapp, Dublin, OH (US)

(*) Notice: Subject to any disclaimer, the term of this patent is extended or adjusted under 35 U.S.C. 154(b) by 318 days.

This patent is subject to a terminal disclaimer.

(21) Appl. No.: 16/410,417

(22) Filed: May 13, 2019

(65) Prior Publication Data

US 2019/0262186 A1    Aug. 29, 2019

Related U.S. Application Data

(63) Continuation of application No. 15/052,744, filed on Feb. 24, 2016, now Pat. No. 10,285,867.

(60) Provisional application No. 62/119,999, filed on Feb. 24, 2015.

(51) Int. Cl.
*A61F 13/02* (2006.01)
*A61F 13/00* (2006.01)

(52) U.S. Cl.
CPC .... *A61F 13/0273* (2013.01); *A61F 13/00008* (2013.01); *A61F 13/00017* (2013.01); *A61F 13/00029* (2013.01); *A61F 13/00038* (2013.01); *A61F 13/00059* (2013.01); *A61F 13/00063* (2013.01); *A61F 13/025* (2013.01); *A61F 2013/0028* (2013.01)

(58) Field of Classification Search
CPC ............ A61F 13/0273; A61F 13/00008; A61F 13/00017; A61F 13/00029; A61F 13/00038; A61F 13/00059; A61F 13/00063; A61F 13/025; A61F 2013/0028
See application file for complete search history.

(56) References Cited

U.S. PATENT DOCUMENTS

| | | | |
|---|---|---|---|
| 7,854,716 B2 * | 12/2010 | Schuren | A61F 13/069 602/75 |
| 8,679,047 B2 | 3/2014 | Holt | |
| 10,285,867 B2 * | 5/2019 | Rapp | A61F 13/00017 |
| 2005/0209545 A1 | 9/2005 | Farrow et al. | |
| 2010/0312160 A1 | 12/2010 | Creighton et al. | |
| 2015/0154451 A1 * | 6/2015 | Liu | G01L 5/045 382/111 |
| 2015/0297437 A1 * | 10/2015 | Neuenhahn | A61B 5/4848 601/148 |

* cited by examiner

*Primary Examiner* — Ophelia A Hawthorne
(74) *Attorney, Agent, or Firm* — Business Patent Law, PLLC

(57) ABSTRACT

A pressure-sensing compression bandage having a plurality of pressure sensors provided to indicate the pressures applied by and/or the pressure gradient created by, the applied bandage at various locations along its length when the bandage is applied to a limb or other extremity.

14 Claims, 12 Drawing Sheets

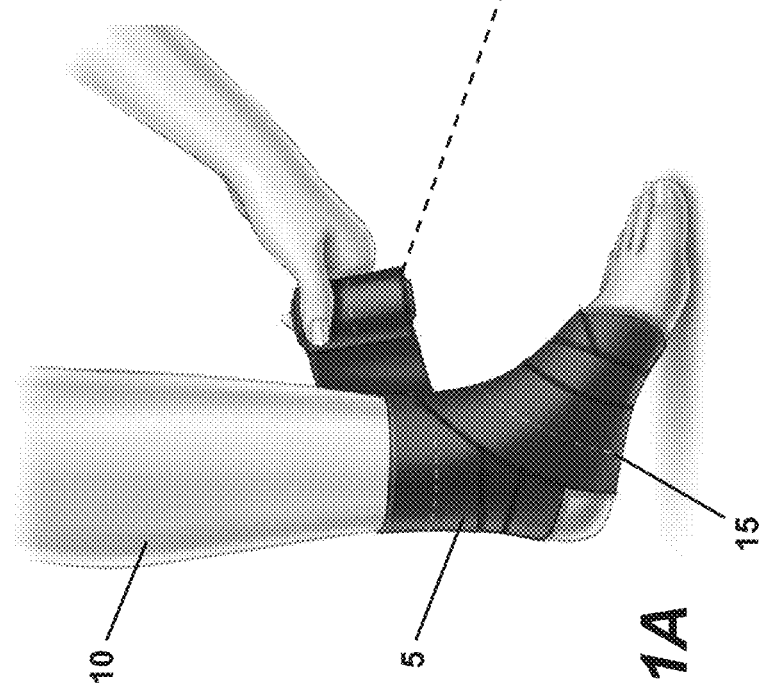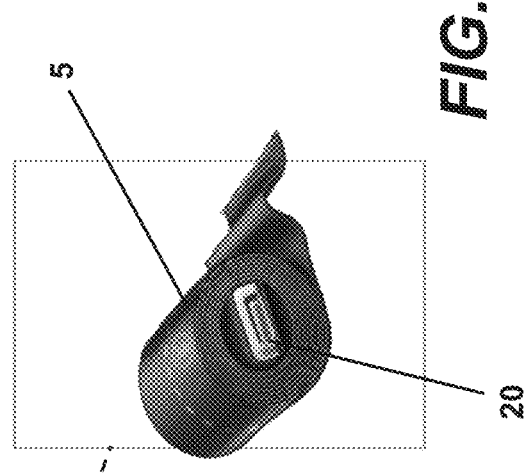

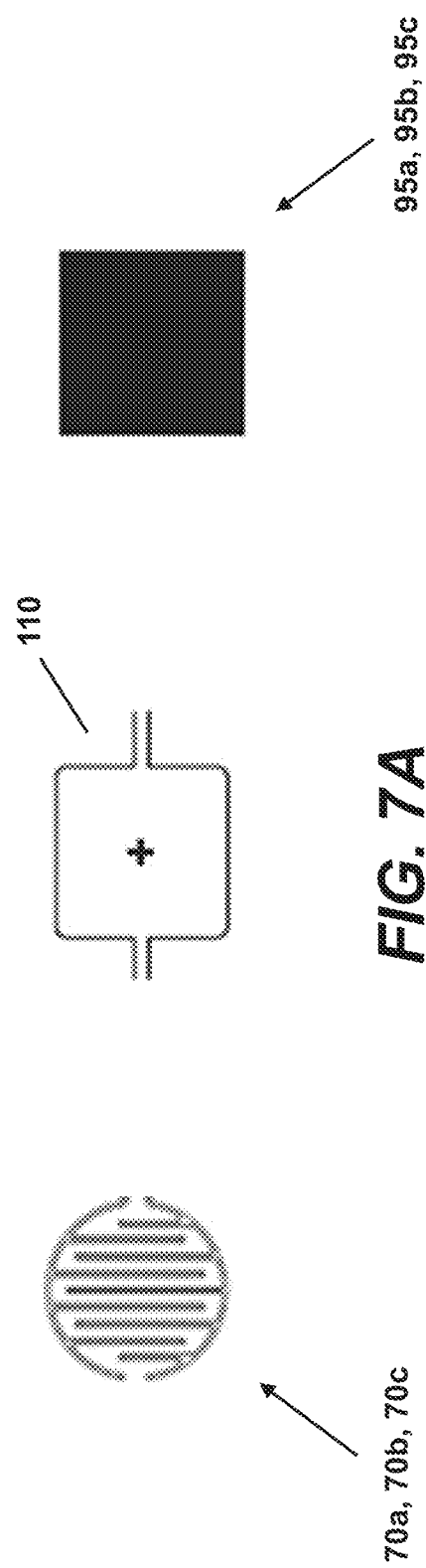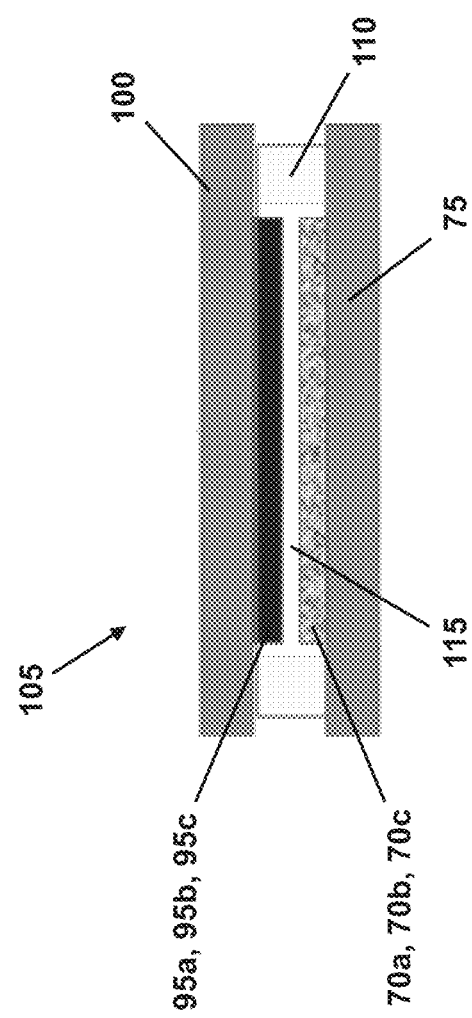

PRESSURE-SENSING COMPRESSION BANDAGE

CROSS-REFERENCE TO RELATED APPLICATIONS

This application claims priority to U.S. patent application Ser. No. 15/052,744, filed on Feb. 24, 2016, now U.S. patent Ser. No. 10/285,867 granted on May 14, 2019, which claims benefit to U.S. Provisional Application No. 62/119,999, filed on Feb. 24, 2015, which is hereby incorporated by reference as if fully recited herein.

TECHNICAL FIELD

Embodiments of this application are directed to pressure-sensing compression bandages.

BACKGROUND

Extremity swelling is a common entity afflicting a large population worldwide. One common cause of extremity swelling is a buildup of excess fluid in the tissue of the extremity. This buildup of excess fluid is referred to generally as edema, and frequently results from an increase in capillary permeability that leads to a stasis of extravascular fluid in the extremity. The increase in fluid extravasation may manifest with dolor (pain), calor (heat), hyperemia, decreased range of motion, and/or swelling. Chronic extremity swelling can have deleterious implications on the healthy maintenance of the surrounding soft tissues and lead to skin break down and ulcers, an ulcer being defined generally as a defect in the skin, often below the knee, that has been present for more than four to six weeks. Such health implications can create significant ongoing economic burdens on a global scale.

Edema may be attributable to multiple pathologies. Two common but not exhaustive sources of edema in the lower extremities are chronic venous insufficiency (CVI) and chronic lymphedema. By clinical definition, CVI results when the venous system of the body can no longer effectively pump blood back to the heart, or otherwise from a disruption in the venous system of blood return to the heart. With respect to the lower extremities, the venous flow travels through three systems or the deep, superficial and communicating venous systems. Blood is moved upwards from the leg to the heart by muscle contraction, such as contractions of the gastrocnemius and soleus muscles of the leg. As a result of gravity, pressures change along the course of the leg when in a standing position. For example, standing pressures at the ankle are usually 90-100 mmHg in the venous system. When walking, the pressures fall quickly to around 20 mmHg but return to normal higher pressures within seconds of movement cessation.

An inability of the body to create such a pressure difference is known as venous hypertension. Venous hypertension leads to the distension of the capillary walls and leakage of various macromolecules from within the capillaries into the dermis. This leads to lipodermosclerosis or the characteristic 'woody' and 'bruised' appearance to the skin, and may ultimately result in the development of ulcers in the skin and even cell death.

Lymphedema results when lymphatic system is unable to recollect interstitial fluid that has escaped the intravascular space. The most common cause of lymphedema worldwide is the Filarioidea round worm parasite, which causes a condition known as filariasis. Other conditions such as congenital deformities, obesity, and radiation can also lead to lymphedema through lymph outflow compromise.

The lymphatic system, among other things, helps to reduce overall pressure in the lower extremities. More particularly, small lymphatic channels similar to veins capture extravasated fluid produced during inflammation and filter the fluid through lymph nodes before returning it to the general body circulation near the heart.

Damage to the valves in this system or chronic inflammation may lead to fluid accumulation in the effected extremity, with an inability to passively reabsorb such fluid. Inflammation leads to changes within the vascular structures, possibly leading to vessel dilation and cellular death.

It is estimated that CVI leading to lower extremity ulceration has an incidence of 1-4.3% of the Western population, and that 3-4% of individuals over the age of 65 manage chronic wounds of the lower extremity attributable directly to swelling and edema. Another report states that the incidence of these problems is as high as 1.2-11.0 persons per 1,000 population. Chronic skin related wounds in the United States affect over 6.5 million people each year.

The actual prevalence of such problems is much higher than indicated above, as the average duration of healing time for ulceration from CVI is reported to be over 12 months. It has also been determined that persons who develop ulcerations from CVI will experience more than ten episodes of such ulceration in his or her lifetime. The 12-month recurrence rate has been estimated to be between 18-28%, with the overall 5-year recurrence rate as high as 78% in this population.

It is estimated that lymphedema disfigures and incapacitates over 120 million people worldwide. More specifically, and as an example, it has been reported that there are between 3-5 million people in the United States affected by lymphedema, approximately 40 million in Brazil and Haiti, and around 300,000 in Canada.

Various neuropathies leading to decreased limb mobility and increased risk for inflammation or swelling also exist. One such exemplary neuropathy is Diabetes Mellitus. There are an estimated 347 million people worldwide with type II Diabetes.

Inflammatory disorders such as rheumatologic diseases or pyoderma gangrenosum can also lead to lower extremity skin problems and edema. Obesity is recognized as effecting 78 million people in the United States without an established incidence of associated lymphedema. Pregnancy is associated with silent thrombosis and increased overall intravascular fluid volumes leading to similar clinical symptoms. Extremity trauma has a high positive correlation to phlebitis and venous thrombosis. Lastly, the geriatric population, in general, has higher rates of immobility, decreased pump and muscle function and dependent lower extremity edema as a consequence.

Skin breakdown and ulceration from the above processes are common. Multiple cycles of healing and repeated ulceration comes with a recurrence rate as high 72%. It is common to see related ulcers in patients lasting over 5 years and labeled as refractory to conventional therapies.

Furthermore, the psychological effects of extremity edema, ulceration and lymphedema are detrimental to the overall quality of life. Psychological distress leading to anxiety, depression and mood disturbances is well documented and contributes to significant extraneous health care costs. There is also an associated public fear, general stigma and perceived marginalization, all of which may lead to social isolation, societal withdrawal and ultimately decreased functional work and productivity. Moreover, lack of social support and correlation to concomitant lack of health care further drives up costs.

With respect to costs, chronic wound care in the United States alone is estimated to cost over 25 billion dollars. The average monthly cost for an American with an open wound is $4,095. Of the aforementioned 25 billion dollar amount, the treatment of chronic venous ulcer wounds alone is believed to cost approximately 1-2 billion dollars, with the direct cost of treating each patient amounting to approximately $30,000 per year in the United States. Worldwide, CVI and venous ulcers leads to expenditures of over 7 billion per year in health care costs.

The treatment and management of edema, lymphedema or any other cause of increased extravascular fluid extravasation or tissue compromise in an extremity is usually initially approached through extremity elevation. The recommended anecdotal guidelines involve raising legs or arms above the heart level for 30 minutes, three to four times a day. As a result, swelling normally subsides over extended periods of time and general microcirculation improves. However, and as should be apparent, a treatment program consisting of such extremity elevation is not always practical.

The next minimally invasive approach to the treatment of such extremity problems involves compression through bandages, garments, or hosiery. The classification system used to describe this modality depends on the clinical scenario and the associated level of pressure being applied by the compression article.

Hosiery or compression stockings and other garments, commonly known as Ted Hose, involve compression through 1 or 2 layers. In the case of a leg, Class 1 garments involve light support and provide 14-17 mmHg of pressure at the ankle. Class 1 garments are used to treat varicose veins. Class 2 garments provide medium support, and produce pressures of 18-24 mmHg at the ankle. This class of garments is used to treat more severe varicosities, and to prevent venous leg ulcers. Class 3 garments provide strong support, or 25 to 35 mmHg of pressure at the ankle. This class of garments is used to treat severe chronic hypertension and severe varicose veins, and to prevent venous leg ulcers.

A parallel therapeutic intervention involves the use of long stretch elastic bandages or spiral wraps. Note that the terms bandage(s) and wrap(s) are generally used interchangeably by the medical profession (the terminology of choice depending mostly on geography) and, therefore, both terms may be used interchangeably herein and both terms are considered to refer generally to any spirally or otherwise wrapped compression device for providing multilayered compression of a limb. The term "bandage", when used herein, is not to be construed in a narrower sense as limited to the treatment of a wound.

Multilayered compression bandages also have a grading system. Class 1 bandages are known as retention bandages, and are used to retain dressings. Class 2 bandages are known as support bandages, and are used to support strains and sprains (e.g., an Ace™ wrap). Other bandages in this category (e.g., the Setocrepe bandage from Mölnlycke) can apply mild to moderate compression. Class 3a is subcategorized as light compression. Bandages in Class 3a (e.g., the Elset bandage from Mölnlycke) exert 14 to 17 mmHg of pressure at the ankle when applied in a simple spiral. Class 3b bandages apply moderate compression. Bandages in Class 3b (e.g., the Granuflex® adhesive compression bandage from ConvaTec) apply 18 to 24 mmHg of pressure at the ankle when applied as a simple spiral. Class 3c bandages are defined as generating high compression. Bandages in Class 3c (e.g., the Setopress bandage from Mölnlycke or the Tensopress bandage from Smith and Nephew) apply 25 to 35 mmHg of pressure at the ankle when applied as a simple spiral. Lastly, Class 3d bandages deliver extra high compression. Bandages in Class 3d apply up to 60 mmHg of pressure at the ankle when applied as a simple spiral.

Yet another category of bandages includes the rigid or short stretch bandages which, when used on a leg, are designed to provide sustained pressures of 40 to 45 mm Hg at the ankle, graduating to 17 mm Hg below the knee. Pneumatic compression is another non-invasive intervention that is gaining greater acceptance for use in the improvement of lower extremity circulation, and is most often used to prevent deep venous thrombosis in incarcerated or immobile patients. In pneumatic compression, a pump actively creates air pressure to mechanically force the fluids of the extremity in a particular direction.

Ultimately, the four-layer multi-component compression bandage system (four-layer bandage) is still regarded as the gold standard initial compression system to treat venous leg ulceration and lower extremity edema. It has been found that compression increases ulcer-healing rates. Compression alone is superior to a moist interactive dressing without compression. High compression regimens are more effective than low compression. Lastly, adherence to high levels of compression after healing reduces the rate of recurrence.

It can be understood from the foregoing observations that limb swelling due to CVI, lymphedema, etc., as well as the problematic conditions that may result therefrom, is prevalent, costly, and may be extremely debilitating. While compression bandages and their use are known and accepted for the treatment of swelling, improvements therein are need to optimize treatment success and to minimize or prevent injuries that may be caused by the improper application of compression bandages. Exemplary devices and methods of this application embody such improvements.

SUMMARY

Exemplary embodiments described in the present application are directed to improved compression bandage devices and their methods of use in the treatment of swelling and/or other conditions. There have been heretofore few tangible advances in this technology since the concept of spiral compression bandages was originally described over 200 years ago.

Currently, trained health care providers or equivalent personnel must apply layered spiral compression bandages consistently and appropriately. When a non-graded application is undertaken, results can be harmful to the patient as detrimental effects can occur with incorrect application. For example, applying a compression bandage too loosely in one region may cause tissue fluid to move distally as opposed to a desired proximal direction toward the heart. In contrast, applying a compression bandage too tightly may result in discomfort, non-compliance and even tissue compromise. Limb ischemia and resultant amputation have been reported in this regard.

With respect to the leg, these difficulties can be attributable at least in part to the ankle-calf disproportion, i.e., narrow ankles and wide calves. Many studies have shown that application training is necessary and a learning curve exists for most applicators—with experience providing the most reproducible results.

In accordance with the accepted Law of Laplace, an evenly applied pressure will be higher in the ankle than the calf due to the radius (correlation to girth) of the location being wrapped. This is a major problem with hosiery, as the 'one size fits all' concept does not translate globally. Rather, arriving at a desired universal graded pressure distribution would require an established pressure-girth profile. Unfortunately, people have extremity thicknesses that change with both gender and age—making the successful use of a universal graded pressure distribution virtually impossible.

Exemplary device and method embodiments described herein remove any guesswork and analysis of limb morphology by allowing a greater population of consumers and patients access to more consistent pressure application. More particularly, exemplary device and method embodiments of the invention improve upon conventional compression bandages and the use thereof by providing a comfortable, reusable, and low cost, pressure-sensing compression bandage that is able to deliver consistent and observable pressure readings to a user through user-friendly interfaces. Both patients and health care providers will benefit from the ease of application and use resulting from the pressure interrogation and reporting provided by said devices.

Exemplary device embodiments are, generally speaking, multilayered, pressure-sensing compression bandages that allow a user to provide graded pressure to an extremity during bandage application. The creation of a graded pressure is produced by applying the same compression evenly along the extremity as the girth of the extremity changes. Resultantly, for example, the same applied compression over the calf will provide less transmitted pressure than the ankle, which has less overall girth.

The exemplary compression bandage embodiments described herein preferably include multiple layers, such as but not limited to a comfort layer to be located at or near the skin surface, an elastic compression layer, and a sensor layer. An optional custom insert/layer may also form a localized, intermittent or continuous layer along the interior surface of the comfort layer for the purpose of, without limitation, fluid absorption, improving wound or scar healing, or other therapeutic purposes. One exemplary compression bandage embodiment may be comprised of five distinct layers: a therapeutic innermost layer, a comfort layer, a pressure/ temperature sensing area disposed along the comfort layer, a graded elastic layer, and an outer layer containing markings/colors to guide a user in creating a proper overlap of the compression bandage during application. Each of the aforementioned and exemplary pressure-sensing compression bandage layers may be comprised of various materials, as will be described in more detail below.

A sensor assembly is also present and preferably includes a series of spaced apart pressure sensors that are attached to or embedded in a mesh material or some other suitable fabric, etc., such as for example, to/in the material forming the comfort layer. Alternatively, the sensors may be trapped between one material layer and an adjacent material layer (e.g., a comfort layer and overlying elastic compression layer, or an outer layer and an underlying elastic compression layer).

The sensors of an exemplary compression bandage are preferably arranged such that the sensors will be located at spaced apart intervals along the length of an extremity as the compression bandage is applied to the extremity. Consequently, the sensors are able to detect and report the pressures applied by the bandage at various locations along the length of the extremity.

In use, the sensors will report pressure readings to a monitor-controller, which may be a fixed device in a clinic, etc., or a portable device that may be small enough for handheld use and/or for wearing or carrying by a patient to which an exemplary pressure-sensing compression bandage is applied. In an exemplary embodiment, a monitor-controller may be removably attached to a pressure sensing compression bandage and connected to the sensors and associated circuitry thereof after application of the bandage to a patient.

An exemplary monitor-controller may display readings from the pressure sensors in any manner that allows a user to understand the pressure readings or the pressure gradient produced by the pressure-sensing compression bandage. For example, and without limitation, a pressure gradient may be displayed in various colors that represent under pressure, ideal pressure, and excess pressure areas or zones along the length of the applied pressure-sensing compression bandage.

The monitor-controller may include a microprocessor, memory, communications elements, corresponding programming and/or software, and/or any other components necessary to produce the desired operation and interaction between the monitor-controller and a pressure-sensing compression bandage. Communication between the monitor-controller and a pressure-sensing compression bandage may be wired or wireless in nature. A mobile device application may also be provided on a mobile device and may communicate with the monitor-controller, accept data from the monitor-controller, or comprise the monitor-controller and its functionality. For example, the sensors on the pressure-sensing compression bandage may communicate wirelessly with a mobile device to display the pressure gradient and/or other information.

An alerting function may also be provided if the pressure applied by an associated pressure-sensing compression bandage drops below or exceeds some preset ideal pressure or range of pressures. Alerts may be provided to the patient and/or to a health care provider. Pressure data may be recorded.

Other aspects and features will become apparent to those skilled in the art upon review of the following detailed description of exemplary embodiments along with the accompanying drawing figures.

BRIEF DESCRIPTION OF THE DRAWINGS

In the following descriptions of the drawings and exemplary embodiments, like reference numerals across the several views refer to identical or equivalent features, and:

FIG. 1A illustrates one exemplary embodiment of a pressure-sensing compression bandage being applied to an extremity in the form of a human lower leg;

FIG. 1B is an enlarged view of the pressure-sensing compression bandage of FIG. 1A in a rolled up and pre-applied form;

FIG. 7A schematically represents the various unassembled components of an exemplary sensor assembly construction of one exemplary pressure-sensing compression bandage;

FIG. 7B schematically illustrates the components of FIG. 7A in an assembled state;

DETAILED DESCRIPTION OF EXEMPLARY EMBODIMENTS

Figure 2:
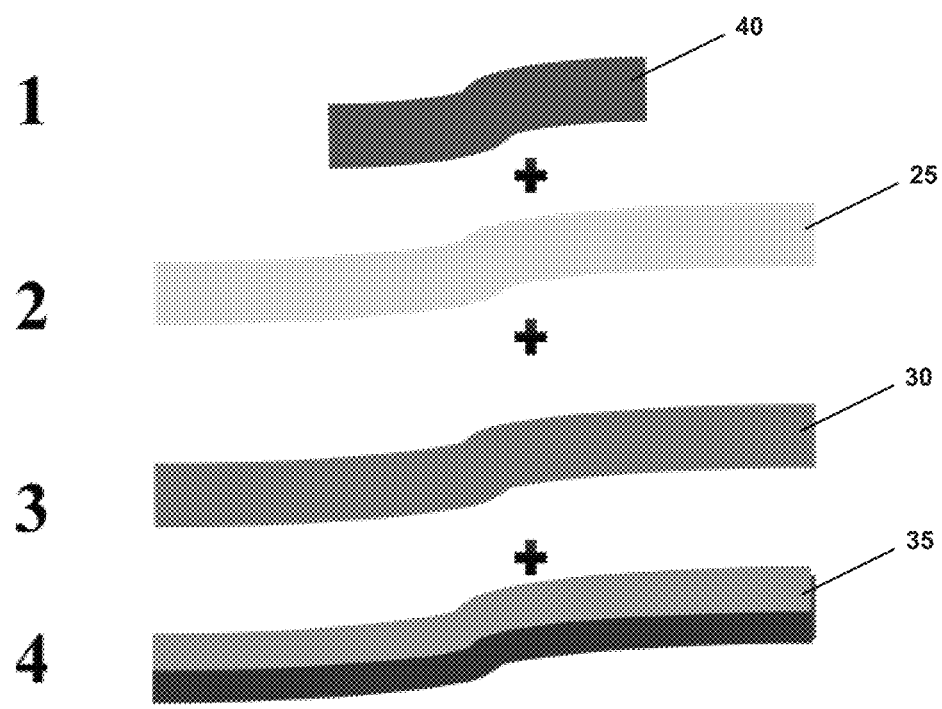
FIG. 2 is an exploded view depicting various possible layers of one exemplary pressure-sensing compression bandage.

FIG. 1A illustrates the application of one exemplary embodiment of a pressure-sensing compression bandage 5 to a limb in the form of a human lower leg 10. As shown in FIGS. 1A-1B, the pressure-sensing compression bandage 5 may be initially provided in a rolled up form for easy storage and application. The pressure-sensing compression bandage 5 may include an overlap indicator 15 (as represented by the dashed line) that assists the applier of the pressure-sensing compression bandage with proper wrapping thereof. The inclusion and use of an overlap indicator/marking is described in more detail below.

As also depicted in FIG. 1B, the pressure-sensing compression bandage 5 may include a monitor-controller 20. In this example, the monitor-controller 20 may be employed to provide a user with post-application information relating to, for example, the pressure applied to the limb 10 by the pressure-sensing compression bandage, the skin temperature along different points of the limb underlying the pressure-sensing compression bandage, etc. As shown in FIG. 1B, the monitor-controller may come pre-connected to the pressure-sensing compression bandage 5.

Exemplary pressure-sensing compression bandage embodiments, such as the pressure-sensing compression bandage 5 of FIGS. 1A-1B, preferably include multiple layers, as shown in FIG. 2. These layers may include but are not limited to a comfort layer 25 to be located at or near the skin surface, an elastic compression layer 30, and an outer layer 35. An optional custom insert 40—such as a therapeutic insert—may form a localized, intermittent or continuous layer along the interior (skin-facing) surface of the comfort layer 25. Other numbers and combinations of layers are possible in other embodiments. For example, another exemplary pressure-sensing compression bandage embodiment may be comprised of five distinct layers: a therapeutic innermost layer or insert, a comfort layer, a pressure/temperature sensing layer disposed along the comfort layer, a graded elastic layer, and an outer layer containing markings/colors to guide a user in creating a proper overlap of the pressure-sensing compression bandage during application.

The comfort layer of exemplary pressure-sensing compression bandage embodiments may be comprised of, for example, one or combinations of cotton, foam, gel, silicone, elastane (e.g., Lycra®), nylon, spandex, viscose, velour or other suitable and preferably stretchable materials. Exemplary comfort layers may also include on the skin-facing surface thereof a coating, stripe or stippled pattern of an adhesive, such as but not limited to a silicone adhesive, to prevent slippage and thereby allow the associated pressure-sensing compression bandage to be positioned on a limb without malpositioning or movement of the bandage. A silicone or similar adhesive can produce mild adhesion even when placed against macerated skin or exudates from a chronic wound. The applied silicone or other adhesive thickness should be thin enough (e.g., less than 1 mm) so as not to detrimentally affect the overall elasticity of the pressure-sensing compression bandage.

Figure 3:
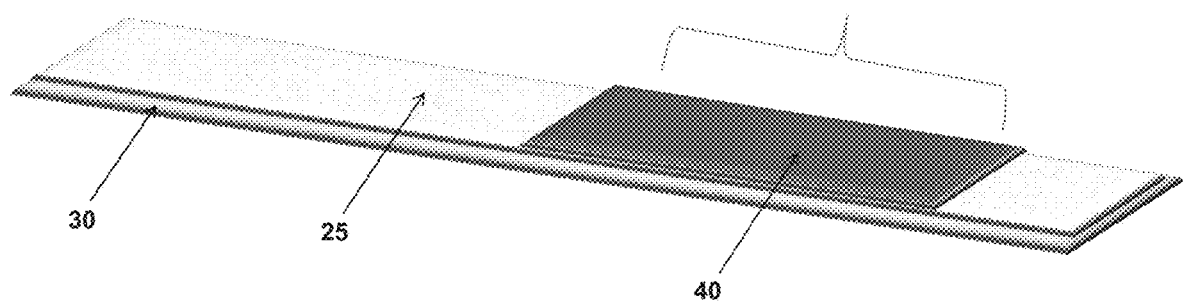
FIG. 3 is an unrolled view of several layers of one exemplary pressure-sensing compression bandage illustrating the presence of a comfort layer that is sandwiched between an inner, targeted therapeutic insert, and a superjacent elastic layer.

As mentioned above, a custom insert may form a localized, intermittent or continuous layer along the interior surface of the comfort layer. As shown in FIGS. 2 and 3, the custom insert of the exemplary pressure-sensing compression bandage 5 is a therapeutic insert 40. The therapeutic insert 40 may be positioned along a $1^{st}$, $2^{nd}$, and/or final $3^{rd}$ of the pressure-sensing compression bandage to allow for wound area coverage along all possible positions on the treated limb. The therapeutic insert 40 may include a mild adhesive on its back side to facilitate retention on the comfort layer 25 while also permitting removal, replacement or repositioning of the insert. Although not likely necessary, the therapeutic insert 40 may be a therapeutic layer that covers the entire or substantially the entire interior surface of the comfort layer 25.

The therapeutic layer may carry or be impregnated with various materials such as, but not limited to, silicone and/or a steroid to aid in scar healing, zinc to aid in wound healing, an antimicrobial (e.g., silver) to reduce bacterial load, alginate to assist with fluid absorption, an enzymatic and/or a biologic.

As described above and illustrated in FIG. 2, exemplary pressure-sensing compression bandage embodiments include at least one, and preferably a plurality, of pressure sensors. In the schematically-depicted pressure-sensing compression bandage construction of FIG. 2, the sensors are indicated as being carried on or embedded in the comfort layer 25, such that the sensors are in close proximity to the skin of a limb subsequent to the pressure-sensing compression bandage being applied thereto. However, it may also be possible to attach, embed or otherwise associate the sensors with another layer of a given pressure-sensing compression bandage. Alternatively, the sensors may be part of a separate sensor layer, which may include a mesh material, or some other suitable fabric or other material that is compatible with the sensors and their attachment thereto or embedment therein.

The elastic compression layer of exemplary pressure-sensing compression bandages may be comprised of, for example and without limitation, polyurethane, methylmethacrylate, polyethylene, silicone, polyvinylchloride, polyester, rubber or any other suitably stretchable material. Preferably, but not necessarily, the material forming the elastic layer can be stretched up to 20%, with return of form following stretch.

The elastic compression layer of exemplary pressure-sensing compression bandages may also contain antimicrobial substances such as zinc oxide or chlorhexidine. When present, chlorhexidine may be bound to the elastic material and used to reduce microbial load when placed in a contaminate field or wound. Chlorhexidine may also be placed in the adhesives that bind the layers of an exemplary pressure-sensing compression bandage so as to impart both bacteriostatic and bactericidal properties to the bandage. Chlorhexidine may also be used in a therapeutic layer in the form of a dressing such as seen in Chlorderm (Entrotech Life Sciences, San Francisco, Calif.).

Figure 4:
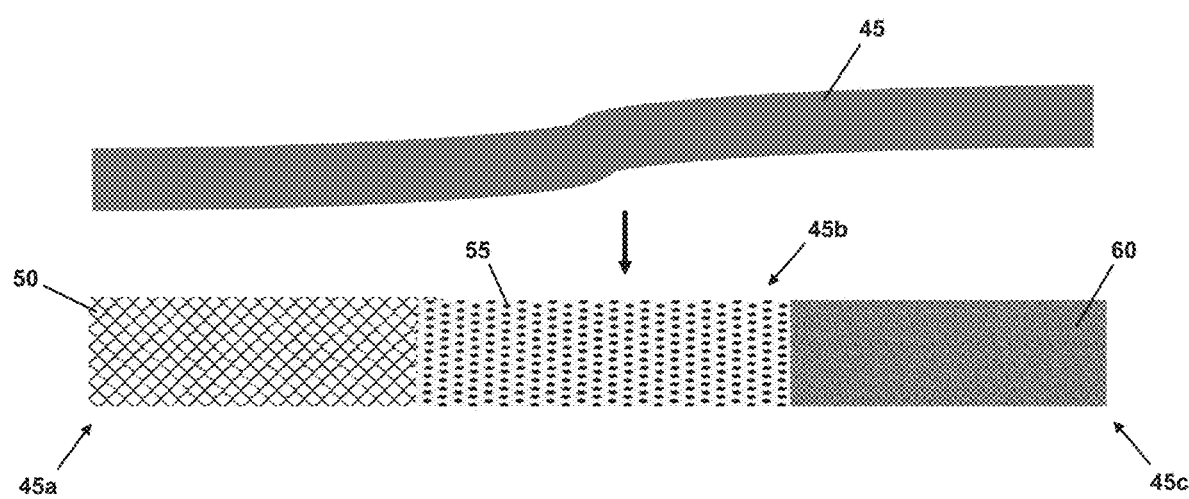
FIG. 4 is a detailed view of the construction of an exemplary elastic layer of one exemplary pressure-sensing compression bandage.

One exemplary construction of an elastic layer 45 of a pressure-sensing compression bandage is schematically represented in FIG. 4. In this embodiment, the material of the elastic layer differs in construction over its length. Particularly, this exemplary elastic layer 45 includes three areas 45a, 45b, 45c of differing elasticity. In this example, the three areas 45a, 45b, 45c of differing elasticity are located to respectively span the distance between the foot and the knee of a human leg when the pressure-sensing compression bandage is applied thereto, with the area 45c of lowest elasticity located near the foot and the area of highest elasticity 45a located near the knee. Other elastic layer constructions are, of course, also possible.

The areas 45a, 45b, 45c of differing elasticity are produced, in this exemplary embodiment, by selectively imparting the elastic material with perforations of different sizes and or number. The spacing and number of perforations may be sequentially increased or decreased to change the amount of stretch in the elastic layer. More perforations will create less tension with even application than the portion of the garment that has less perforations with the equivalent applied tension. For example, in the elastic layer 45 embodiment represented in FIG. 4, diamond perforations 50 of larger size and/or frequency are applied to the area of elasticity 45a that will be closest to the knee portion of the pressure-sensing compression bandage, elliptical perforations 55 of slightly smaller size and/or frequency are applied to the intermediate area 45b, and yet smaller or less frequent perforations 60 of some shape are applied to the area of least elasticity 45c that will be closest to the foot portion of the pressure-sensing compression bandage. Other perforation shapes may also be possible, however, it is noted that the use of elliptical or diamond-shaped perforations ensures that with stretch, there is no bunching of the materials at the ends of the perforation that might limit user comfort. It has been determined that resulting pressures of between, for example, 0 mm Hg and 60 mm Hg are achievable when employing such a technique to manipulate the elasticity of the elastic layer material.

The outer (comfort/application) layer of exemplary pressure-sensing compression bandages may be comprised of, for example and without limitation, one or a combination of elastane (e.g., Lycra®), polyester, nylon, cotton, velour, and carbon, or one or a combination of other suitable materials. As described in more detail below, the outer layer may also include design features that facilitate consistent and reproducible application of the associated pressure-sensing compression bandage.

A more detailed understanding of the sensor technology of one exemplary pressure-sensing compression bandage may be achieved by referring to the previous disclosure in combination with FIGS. 5-7B. As previously explained, exemplary pressure-sensing compression bandages preferably include a series of spaced apart pressure sensors that are attached to or embedded in a comfort layer (or another bandage layer) or a separate sensor layer comprising a mesh material or some other suitable fabric, etc. Alternatively, the sensors may be trapped between one material layer and an adjacent material layer (e.g., a comfort layer and an overlying elastic compression layer).

Figure 5:
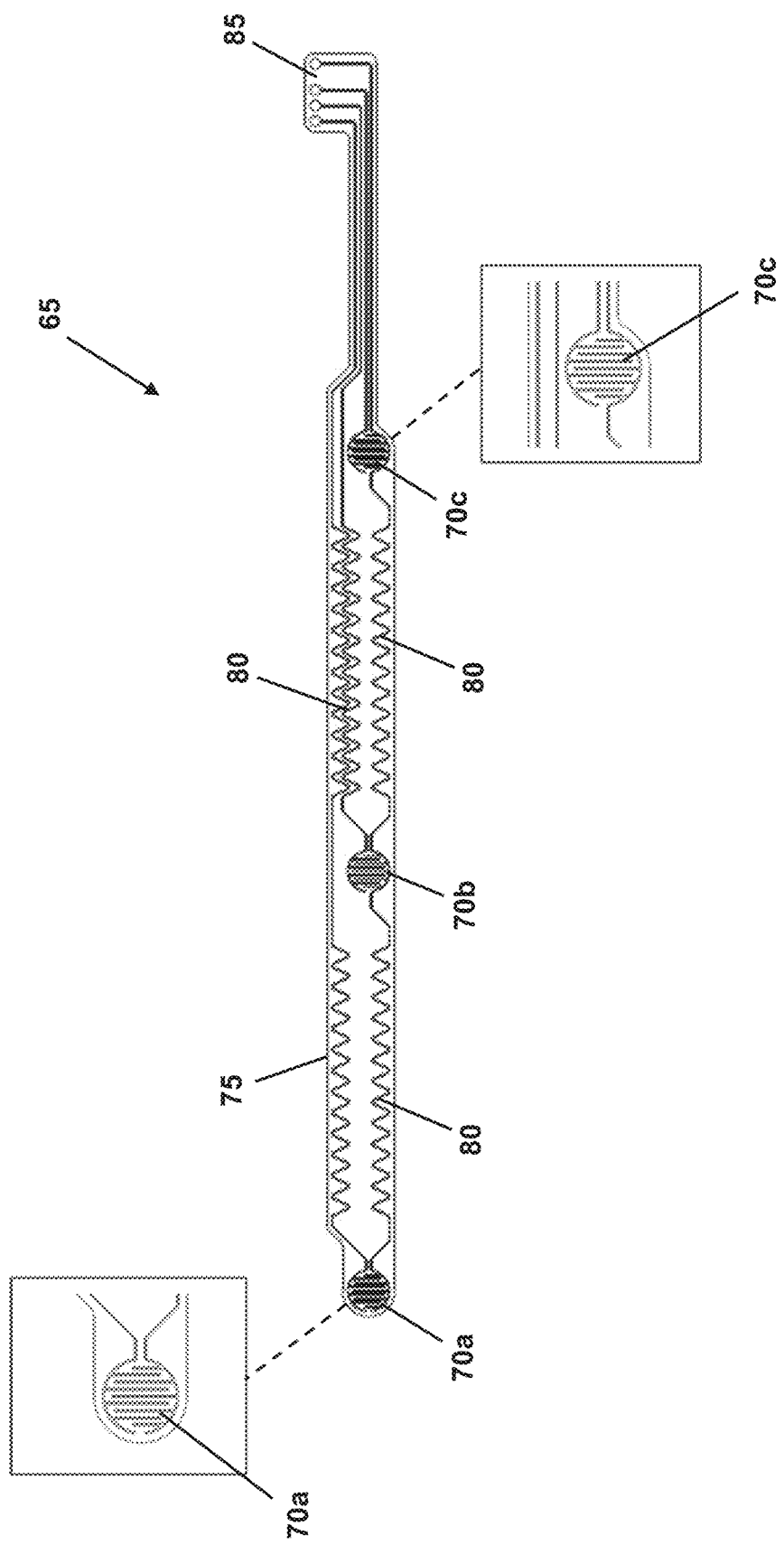
FIG. 5 schematically illustrates an exemplary sensor circuitry layout of one exemplary pressure-sensing compression bandage sensor assembly.
Figure 6:
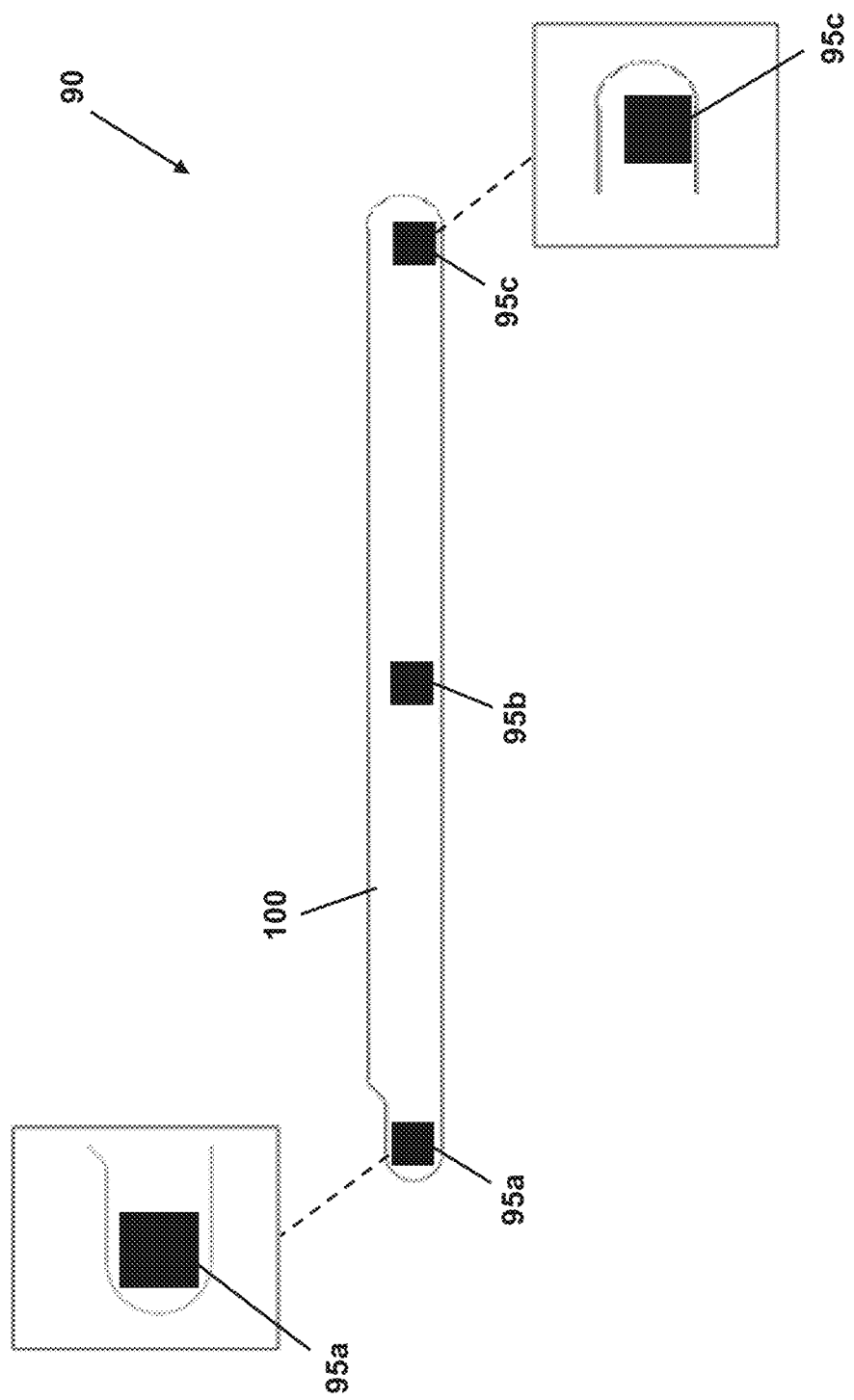
FIG. 6 schematically illustrates an exemplary receptor circuitry layout of one exemplary pressure-sensing compression bandage sensor assembly.

FIGS. 5-6 schematically represent the layout of cooperating circuitry portions of one exemplary sensor assembly of an exemplary pressure-sensing compression bandage. It can be understood from FIGS. 5-6 that sensors are arranged such that as an associated pressure-sensing compression bandage is wrapped around an extremity (e.g., a human leg as indicated in FIG. 1), the sensors will be located at spaced apart intervals along the length of the extremity. Consequently, the sensors are able to detect and report the pressures applied by the pressure-sensing compression bandage at various locations along the length of the extremity (e.g., the foot, ankle, calf, and knee). The number of sensors utilized and the spacing between sensors may vary depending on, for example, the length of the pressure-sensing compression bandage, the length of the extremity to which the bandage will be applied, and the number of different areas along the extremity for which a pressure reading is desired.

As can be understood from FIGS. 5-7B, this exemplary sensor assembly includes various circuitry, which cooperates to produce the desired pressure (and possibly temperature) readings during use of an associated pressure-sensing compression bandage. The sensor assembly may reside on the comfort layer of an exemplary pressure-sensing compression bandage, but other locations are also possible, as explained above. Referring to FIGS. 5-6, it may be observed that three spaced apart sensors are used in this exemplary embodiment.

In this particular example, the included pressure sensors are of a force sensing resistor (FSR) type. The resistance of a FSR will vary in accordance with the amount of pressure that is applied to its sensing area. Therefore, a FSR is well-suited to measuring pressures or changes in pressure created by the application of a compression bandage to a limb/extremity. Furthermore, a FSR type sensor may require less than 5V to operate—meaning that power requirements are minimized. While this exemplary sensor assembly utilizes a FSR, it should be realized that other types of sensors are also usable, such as but not limited to, sensors of piezoelectric or strain gauge design.

While FSRs may be obtained in pre-existing form, the FSR sensors used in this particular example are created by printing the components thereof onto a substrate using a conductive polymer or other conductive material in the form of an ink. When used, such an ink may be comprised of, for example, a conductive polymer such as but not limited to polyacetylene, polypyrrole, or polyaniline, a piezoresistive substance, or a dielectric material. A suitable conductive ink may also be comprised of silver, silver chloride, carbon, or other materials that can be screen or laser printed onto substrates. An example of a latter type of such an ink is the CI-1036 silver ink distributed by Engineered Conductive Materials, in Columbus, Ohio.

The substrate of such an embodiment may be comprised of a variety of materials including but not limited to fabrics and films. In the illustrated exemplary embodiment, the substrate employed is a thin film of polyethylene terephthalate (PET).

One portion 65 of the provided exemplary sensor assembly circuitry is schematically illustrated in FIG. 5. As shown therein, an active area (i.e., a pattern of conductors) 70a, 70b, 70c of each FSR sensor is printed, such as described above, onto a first PET substrate 75. The active areas 70a, 70b, 70c are placed in electrical continuity with corresponding flexible electrical conduits 80 that may also be created by the printing thereof onto the PET substrate 75. The flexible electrical conduits 80 act as the leads that will carry signals produced by the assembled pressure sensors to a connector 85, which is adapted to couple the sensors to a monitor-controller or other display and/or control device. The flexible nature of the electrical conduits 80 ensures that there is no increase in resistance and resultant loss of sensitivity at the sensor-circuit interface. The flexible nature of the electrical conduits 80 also eliminates any discomfort that might be imparted to a user if the conduits were comprised of metal wires and, unlike wires, are far less limiting on the elasticity possessed by the associated pressure-sensing compression bandage.

A cooperating portion 90 of the provided exemplary sensor assembly is schematically illustrated in FIG. 6. As shown therein, a series of spaced apart receptor areas 95a, 95b, 95c are located on a second PET substrate 100. The receptor areas 95a, 95b, 95c are located and arranged on the second substrate 100 to correspond with the active areas 70a, 70b, 70c on the first substrate 75 upon assembly of the sensors (as described in more detail below). As with the active areas 70a, 70b, 70c and the electrical conduits 80 of the first portion of the sensor assembly, the receptor areas 95a, 95b, 95c may be printed onto the second PET substrate 100. Other known techniques for creating the receptor areas 95a, 95b, 95c on the second substrate 100 are also possible.

A better understanding of the assembled exemplary sensor assembly described and shown herein may be had by further reference to FIGS. 7A-7B. As may be observed therein, the first portion 65 and second portion 90 of the sensor assembly 105 are located to one another in a mirrored relationship such that the active areas 70a, 70b, 70c on the first substrate 75 and the receptor areas 95a, 95b, 95c on the second substrate 100 are aligned, in close proximity, and facing each other, to thereby form individual pressure sensors.

A separator layer 110 is located between the first substrate 75 and the second substrate 100. The separator layer 110 is of a thickness selected to produce an air gap 115 between the active areas 70a, 70b, 70c and corresponding receptor areas 95a, 95b, 95c of each pressure sensor when an associated pressure-sensing compression bandage is in a relaxed (unapplied state). The air gap 115 ensures that the sensors will not produce pressure readings until the associated pressure-sensing compression bandage is wrapped around a limb and applies a pressure to the underlying limb tissue.

As illustrated in FIGS. 7A-7B, the separator layer material surrounds but does not intrude into the space between the active areas 70a, 70b, 70c and corresponding receptor areas 95a, 95b, 95c of each pressure sensor. The separator layer 110 may be comprised of a non-conductive foam, polyurethane, or other compressible material that will permit compression of the pressure sensors upon application of an associated pressure-sensing compression bandage to the limb/extremity of a user. The separator layer material may be air permeable and/or may be vented to permit the escape of any air trapped between the active areas 70a, 70b, 70c and corresponding receptor areas 95a, 95b, 95c of the pressure sensors upon compression thereof.

Once the various electrical components of the pressure sensors are printed or otherwise applied to the substrates 75, 100, the substrates may be die cut, laser cut, or otherwise trimmed if desired to minimize the size of the sensor assembly 105. It may also be possible to so dimension the substrates 75, 100 prior to applying the electrical components thereto.

Once the first portion 65 and second portion 90 of the sensor assembly 105 are properly arranged with respect to one another, with the separator layer 110 appropriately positioned therebetween, the adjacent faces of the substrates may be joined to produce a sealed, water-resistant sensor assembly. Joining of the substrates 75, 100 may be accomplished by any know technique, such as but not limited to, heat lamination. The sealed sensor assembly 105 may then be properly positioned on and attached to or embedded in a selected layer (e.g., the comfort layer) of an associated pressure-sensing compression bandage. For example, and without limitation, the sealed sensor assembly 105 may be attached to a layer of a pressure-sensing compression bandage by heat laminating one of the PET substrates 75, 100 thereto.

In some exemplary embodiments of a pressure-sensing compression bandage that employs FSR-type pressure sensors, an area of more rigid material (not shown) may be associated with one or both of the active and receptor areas of the FSR. For example, pieces of rigid material may be bonded to or embedded in the substrate(s) to overlie the active areas and/or receptor areas. When present, the rigid material may assist in transferring the compressive forces generated by application of the associated pressure-sensing compression bandage to the pressure sensors.

In operation of the exemplary FSR pressure sensors subsequent to attachment to an associated pressure-sensing compression bandage, wrapping of the bandage around a limb/extremity produces a compressive force that causes a compression of the separator material 110 and applies pressure to the pressure sensors. In the case of a pressure-sensing compression bandage that employs FSR-type pressure sensors, this pressure produces contact between the active areas and receptor areas of the FSRs which alters the resistance thereof. Increased pressure will cause a greater portion of the active area to contact the receptor area of a given FSR, which further reduces the resistance of that FSR. Signals indicative of FSR resistance and changes in FSR resistance are received by a monitor-controller that is connected to the sensor assembly and converted into pressure readings, as is described in more detail below in conjunction with FIGS. 9-11.

In any exemplary pressure-sensing compression bandage embodiment wherein printing is used in the manufacture of the associated pressure sensors, the thickness of the conductive material (e.g., ink) circuitry may be between, for example, 7-15 µm along the circuit length. The electrical resistance associated with such printed conductive circuitry is expected to be extremely low.

Furthermore, printed conductive material circuitry may be applied to a substrate or directly to a bandage layer in a non-linear orientation/pattern, such that stretching of the associated layer of a pressure-sensing compression bandage will not increase the resistance of the circuit, which could undesirably limit the sensitivity of the pressure sensors. Possible, but non-limiting conductive conduit patterns may include a ladder or grid pattern (i.e., horizontal and vertical printing) or a wavy or zig-zag pattern, to allow for stretch in both the horizontal and vertical directions while still permitting maximal conductive material-to-substrate contact.

Printed sensor elements may also be of various configuration and orientation. For example, the active and/or receptor areas of an exemplary FSR sensor may have interdigitating fingers, as shown in FIGS. 5-6. Likewise, the design of a given pressure sensor may be square, circular, serpiginous, or of another shape that helps the sensor to conform to the body part with which an associated pressure-sensing compression bandage will be applied.

In an alternative embodiment, a FSR sensor may be placed on a dome composed of, for example, polyurethane or an equivalent or similar plastic polymer material, to replace the spacer layer of FIG. 7B while still providing a gap between the active and receptor elements of the FSR.

It is typically desirable that a pressure-sensing compression bandage be applied in a spiral with approximately a 50% overlap between turns, as this results in a double layer bandaging at any point, and allows for predicable sustained pressures to be attained. The equation that supports this idea is the Law of Laplace, where P=(TNK)/CW, P represents the sub-bandage pressure (mmHg), T is the bandage tension (kg of Force), C is the circumference of the limb (cm), W is the bandage width (cm), N is the number of layers applied, and K is the constant value of 4620.

Figure 8:
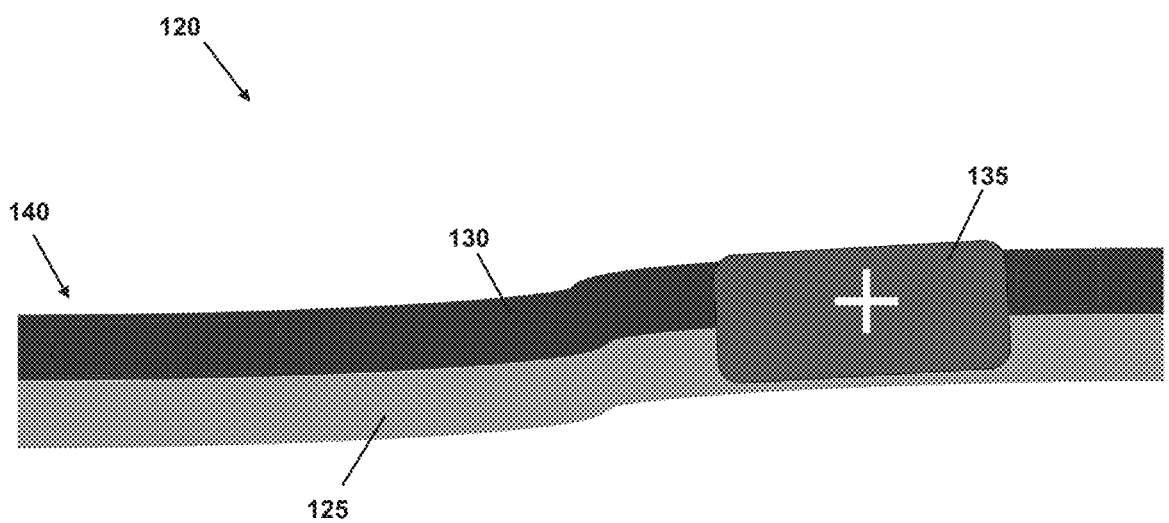
FIG. 8 schematically illustrates one exemplary outer layer of an exemplary pressure-sensing compression bandage.

To this end, FIG. 8 represents one possible construction of an outer layer 120 of an exemplary pressure-sensing compression bandage embodiment that is designed to facilitate proper wrapping. As shown, this outer layer 120 is color coded in a manner where approximately 50% of the outer layer includes a notifying color 125 (green in this example) and, optionally, a mild adhesive, the goal of the user being to cover the notifying layer with each pass so as to ensure a consistent overlap, and the function of the adhesive to retain the overlapped portion of the bandage. The other 50% or so 130 of the outer layer is comprised of another color, such as nude, navy, black, gray or some other color of choice. In this example, a dissimilarly colored (e.g., red) indicator 135 is also present to notify the user of the location of a therapeutic insert so that the insert can be properly positioned over a wound, scar, etc., to be treated. The outer layer may also be labeled 150 to direct proper pressure-sensing compression bandage orientation. For example, one end may be labeled "knee" and the other end labeled "foot" when the bandage is designed for application to a leg. An indication of which end of the bandage is to be applied more tightly may also be provided.

Other outer layer markings or indicators for helping to ensure a consistent overlap is attained when applying an exemplary pressure-sensing compression bandage are also possible. For example, the color coded scheme of FIG. 8 could be replaced with a simple dividing line, as is depicted in FIG. 1

Figure 9A:
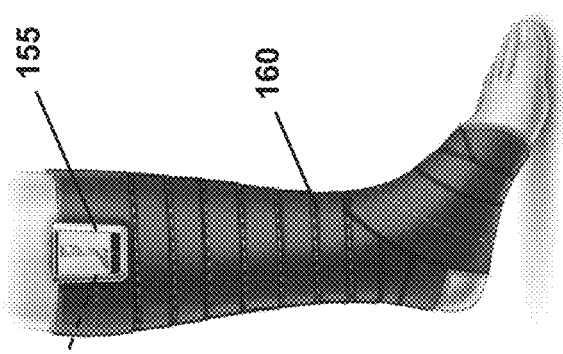
FIG. 9A illustrates one exemplary embodiment of a pressure-sensing compression bandage applied to an extremity in the form of a human lower leg.
Figure 9B:
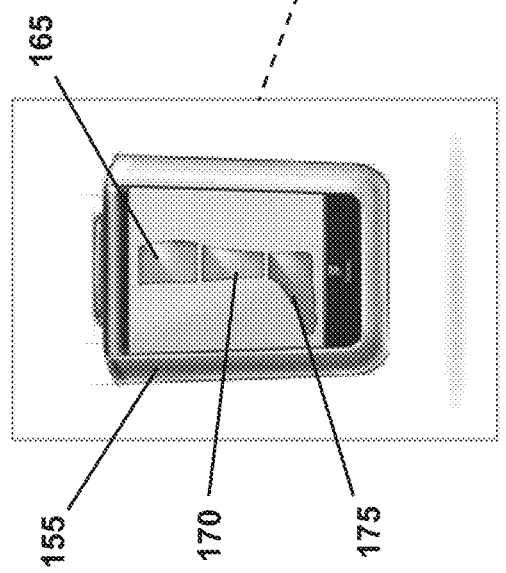
FIG. 9B is an enlarged view of an exemplary monitor-controller that is removably attached to the pressure-sensing compression bandage of FIG. 9A.

In use, the sensors will report pressure readings to a monitor-controller, one non-limiting example 155 of which is represented in FIGS. 9A-9B. An exemplary monitor-controller for use with an exemplary pressure-sensing compression bandage may be a fixed location device, such as in a clinic, etc. Alternatively, and as illustrated in FIGS. 9A-9B, a monitor-controller 155 may be a portable device that is small enough for handheld use and/or for wearing or carrying by a user to which an exemplary pressure-sensing compression bandage is applied.

In the particular example depicted in FIGS. 9A-9B, the monitor-controller 155 is removably (or permanently) attached to an associated pressure-sensing compression bandage 160. The monitor-controller 155 is also connected to the sensor assembly circuitry of the pressure-sensing compression bandage 160, such as for example by a connector like that shown in FIG. 5.

A monitor-controller may display readings from pressure sensors in a manner that allows a user to understand the pressure gradient produced by the pressure-sensing compression bandage. For example, as indicated in FIG. 9A, the pressure gradient may be displayed in various colors that are able to represent under pressure, ideal pressure and excess pressure conditions. For purposes of illustration, each of an under pressure zone 165, an ideal pressure zone 170, and an excess pressure zone 175 are represented on the monitor-controller display of FIG. 9B.

Figure 10C:
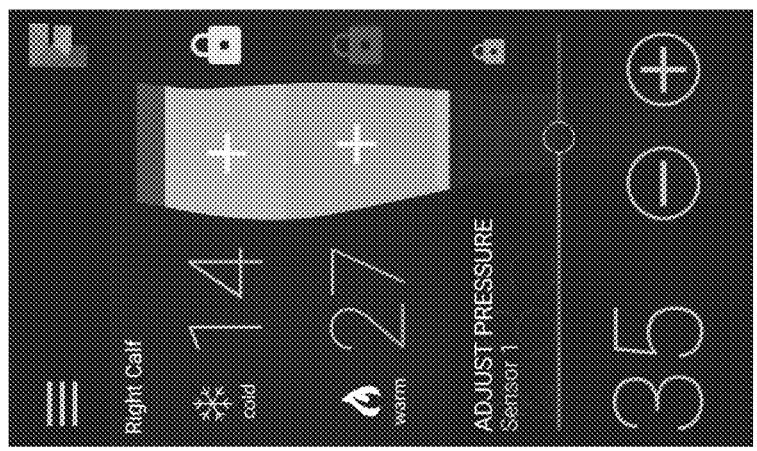
FIG. 10A-10C depict various exemplary display screens that may be presented to a user of a pressure-sensing compression bandage as described herein.
Figure 10B:
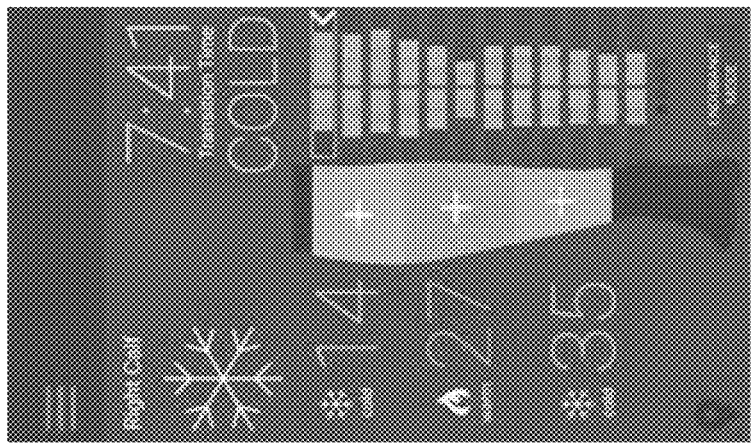
Figure 10A:
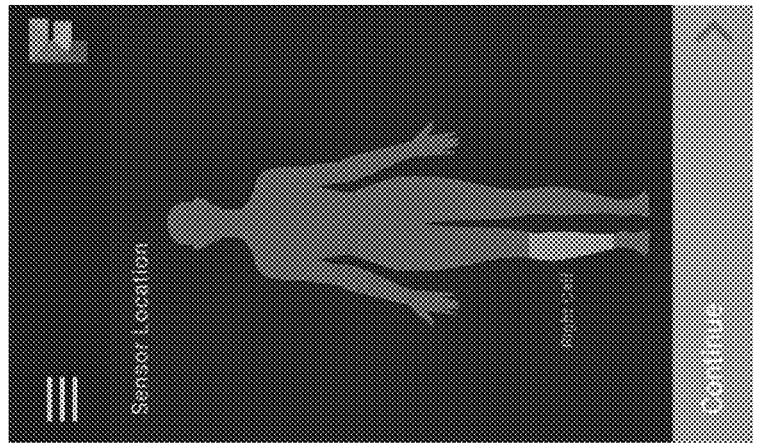

Other exemplary and non-limiting displays associated with a pressure-sensing compression bandage are presented in FIGS. 10A-10C. For example, FIG. 10A represents a basic display of information, such as perhaps a first display screen, which simply indicates to the user that the pressure-sensing compression bandage from which reading are being received is located on the right calf of the user. The display of FIG. 10B is representative of an alternative version of the display of FIG. 9B. That is, different pressure zones are again indicated by different colors, but the associated limb is presented from another perspective and numerical pressure values are also presented for each pressure sensing zone. The display of FIG. 10C is similar to that of FIG. 10C, but also indicates that the sensor nearest the user's foot (Sensor 1) is not reading properly, suggesting that the tightness of the pressure-sensing compression bandage needs to be adjusted along that area of the user's limb. Temperature changes along a pressure-sensing compression bandage may also be displayed.

An exemplary monitor-controller may include a microprocessor, memory, communications elements, corresponding programming and/or software, and/or any other components necessary to produce the desired operation and interaction between the monitor-controller and a pressure-sensing compression bandage. Communication between the monitor-controller and a pressure-sensing compression bandage may be wired in nature, or may be wireless in nature such as via Bluetooth® or another suitable wireless communication protocol such as WiFi or Near Field Communications (NFC).

A mobile device application may also be provided on a mobile device and may communicate with the monitor-controller, accept data from the monitor-controller, or comprise the monitor-controller and its functionality. For example, the sensors on a pressure-sensing compression bandage may communicate in a wired or wireless manner with a mobile device to display a pressure gradient and/or other information (see, e.g., FIGS. 10A-10C). The mobile device may be a mobile phone. However, other mobile devices such as tablets, etc., may also be used in this manner.

An alerting function may also be provided if the pressure applied by an associated pressure-sensing compression bandage drops below or exceeds some preset ideal pressure or range of pressures. Alerts may be provided to the patient and/or to a health care provider by way of a monitor-controller, mobile device, or another device in communication with the sensors of the pressure-sensing compression bandage.

Figure 11B:
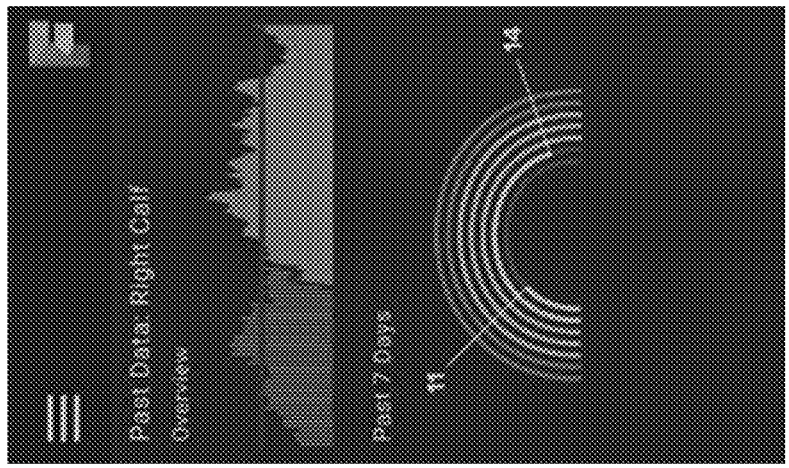
FIGS. 11A-11B depict alternative or additional exemplary display screens that may be presented to a user of a pressure-sensing compression bandage as described herein.
Figure 11A:
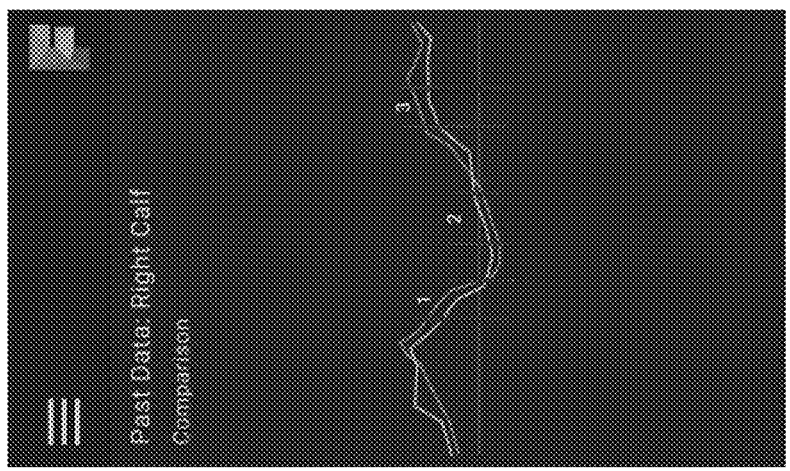

An exemplary pressure-sensing compression bandage may report pressures or pressure gradients in real time—even as the pressure-sensing compression bandage is being applied. As represented by FIGS. 11A-11B, another feature of an exemplary pressure-sensing compression bandage includes the recording, storing and presentation of historical pressure data. The pressure data may be used for any beneficial purpose by the patient and/or a health care provider. For example, historical pressure data may be used to determine if the pressures applied by a pressure-sensing compression bandage remain within an acceptable range throughout the day or if fluctuations occur due to changes in limb size due to activity, temperature, etc.

Exemplary pressure-sensing compression bandages be directed towards quick and efficient monitoring of the pressures under the bandage. An alert may be created when a particular pressure threshold is either exceeded or not met. Alerts can be set to occur, for example, when excessive pressures over 30 mm Hg have existed for greater than two hours, so that such excessive pressure can be alleviated to prevent ischemic conditions. Ranges of acceptable pressures may be customized to an individual to provide maximum comfort while still maintaining graded pressure to help with blood flow up the extremity. This can be observed by the individual or anyone (e.g., a health care provider) who has access to a connected monitor-controller, mobile device and associated application, etc. Pressures can also be tracked, graphed and trended to show how long a given pressure-sensing compression bandage was placed in a beneficial therapeutic range to tailor wound healing rates to an individual. Such information may also be used to gauge how much longer the use of a pressure-sensing compression bandage will be required to improve a particular clinical scenario.

Data stemming from the widespread use of pressure-sensing compression bandage embodiments and associated programs/software may also be mined to provide data for other clinical scenarios. For example, data obtained from the use of pressure-sensing compression bandage embodiments to treat edema, etc., may be used to provide normative data for other applications, such as, but certainly not limited to, the therapeutic use of compression in the treatment of scarring or burn wounds, the use of compression in athletic apparel (e.g., running apparel), or as an indicator of muscle compliance (e.g., when a muscle is optimally 'warmed' up and ready for increased stress) to aid in the prevention of injury.

The proper compression provided by pressure-sensing compression bandage embodiments will improve edema and facilitate wound healing through the mechanical movement of fluid, resulting in the improvement of the venous pump and lymphatic drainage. This can reduce erythrocyte and leukocyte aggregation, with limitation of capillary plugging and vascular compromise to the soft tissue. In short, pressure-sensing compression bandage embodiments permit optimization of compression application while greatly minimizing or eliminating any potential damage to the compressed tissue due to inappropriate wrapping pressure.

While somewhat counterintuitive, the use of a pressure-sensing compression bandage to apply pressure to a limb may also improve blood flow. In fact, studies have shown that $O_2$ partial pressures at the skin increase after compression. Cutaneous blood flow may be reduced, but lowering of edema by compression ultimately increases cutaneous blood flow. Moreover, creating a relative hypoxic state through compression may promote angiogenesis (the forming of blood vessels). It has also been demonstrated that increased fibrinolysis reduces the release of macromolecules into the extravascular space and prevents trapping of mediators important to wound healing.

Pressure-sensing compression bandage embodiments may also be employed in more invasive interventions to address skin breakdown, infection and ulceration, such as by applying topical medications in conjunction with a pressure-sensing compression bandage. Wound debridement can occur passively through autolytic, chemical, mechanical, surgical, and biologic dressings. Examples of autolytic therapies include collagenase, trypsin and fibrinolytic topicals. Fluid exudate from wounds can be managed with alginates and foams. Moist environments to optimize epithelialization can be improved with application of hydrogels, hydrocolloids, and semipermeable films.

Wound healing augmentation can occur with the addition of certain growth factors such as platelet-derived growth factor, tissue plasminogen activator, human recombinant epidermal growth factor, and/or granulocyte-macrophage colony-stimulating factor. Increased vascularity has been shown to improve with the use of papain enriched dressings, Stanozolol, and pentoxifyllin. Biological dressings using living cells both from the individual patient or alloplastic materials to provide tissue engineered skin are also becoming more prevalent. Still in the laboratory phase, but possibly not too far from use, are autogenous stem cell enriched dressings. Examples of application of progenitor cells, such as fat stem cells or ASCs with multiple differential capacities, have shown much wound healing improvement in the animal models.

While the exemplary embodiments described above and illustrated in the drawing figures are directed to a pressure-sensing compression bandage, it is contemplated that the associated technology will be applicable to other devices and treatments. Non-limiting examples of such devices and treatment methodologies include a pressure-sensing cast/splint liner, surgical pressure monitoring, pressure monitoring of intubated patients (e.g., at the occiput of the head or the sacral area), upper extremity compression, post-surgical or plagiocephaly helmets, custom (arm, hand, ankle) sports wraps, prosthetics (e.g., compression of residuum swelling to fit a prosthesis), the treatment of DVT prophylaxis, and in veterinary medicine.

Of particular note in regard to veterinary medicine is the possible use of pressure-sensing compression bandage technology in equine care and maintenance. For example, a pressure-sensing compression bandage may be placed on the leg or thigh of a horse and information about muscle perfusion can be observed. As resistance in the blood vessels change, the overall pressure under the dressing will change. When blood is shunted away from muscles toward vital organ structure (i.e. brain, kidneys), an increase in blood vessel resistance will result in a drop in overall pressure to the system. This may alert a trainer or other care taker that the risk of muscle injury is high. The return of pressures under the pressure-sensing compression bandage to baseline or actually higher pressures than initially seen will notify the caretaker that the muscle is better perfused and warm enough for increased exercise. A large increase in pressure seen under the pressure-sensing compression bandage may indicate that a muscle is fatigued and detrimental byproducts of anaerobic oxygenation (i.e., lactate, $CO_2$, etc.) may lead to muscle strain or injury.

Other contemplated and non-limiting possible uses include the application of a pressure-sensing compression bandage prior to air travel in order to reduce edema as well as to indicate when a user may need to get up and ambulate on long flights. A pressure-sensing compression bandage may also be used under splints to indicate if areas prone to skin breakdown (e.g., the elbow or heel) are experiencing excessive pressure. Pressure changes may also alert a user of excessive pressures and indicate a needed loosening of a splint to prevent pain and discomfort.

Figure 12A:
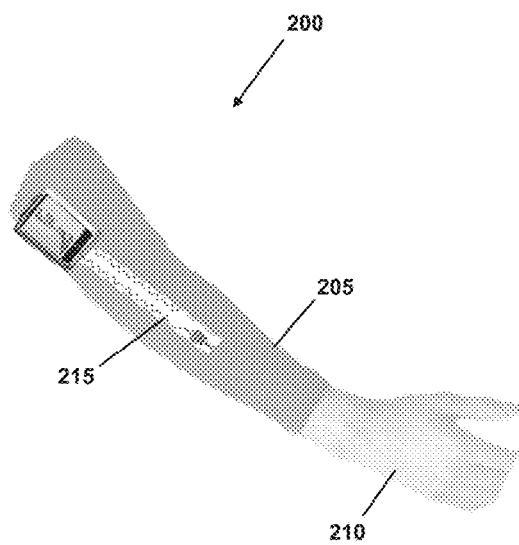
FIGS. 12A and 12B depict alternative embodiments of a pressure sensing device for application to a limb of a user/patient.
Figure 12B:
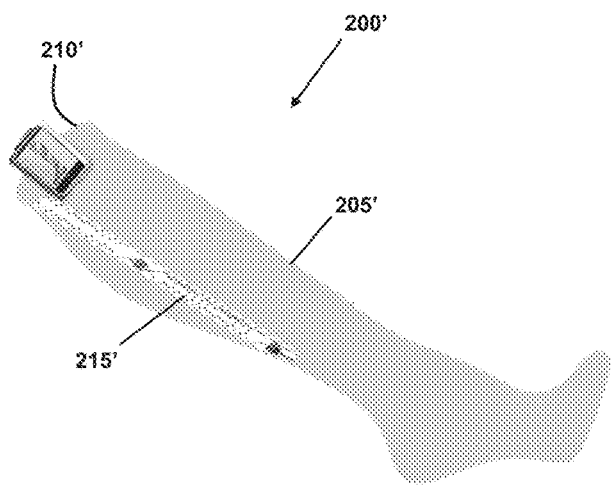

An alternative embodiment of a pressure sensor equipped wearable device 200, 200' is presented in FIGS. 12A-12B. In this embodiment, a sensor-equipped fabric layer 205, 205' is applied to a limb 210, 210' to ultimately position the included sensors 215, 215' over a particular area of interest. For example, in trauma patients such as those sustaining fractures to the lower leg 210' or forearm 210, monitoring muscle compartment swelling is important to reduce the incidence of compartment syndrome. As such, the devices of FIGS. 12A-12B may be fashioned in the form of hosiery or a similar garment that can circumferentially cover a limb. The garment/hosiery is preferably stretchable so as to provide a retentive force upon application that will maintain the desired position of the garment/hosiery.

Pressure sensors may be printed, heat laminated, or otherwise applied to the fabric substrate. Sensors may be positioned and arranged to reside over limb areas to be monitored, such as over muscle compartments. For example, there are three muscle compartments in the forearm, and sensors may be located on the fabric substrate to overlie the anterior, posterior and mobile wad of the forearm to independently observe the swelling in each compartment. In the lower leg, sensors may be similarly placed to reside over the anterior and posterior compartment (overlying 4 compartments). It is also possible to locate multiple sensors over a given area of interest, such as over a given muscle compartment.

Such an embodiment may be left in place while subsequent compressive/elastic dressings are placed. Similarly, such an embodiment may be applied and left in place under a cast or splint.

Although certain exemplary embodiments are described in detail above, the scope of the invention is not considered limited by such disclosure, and modifications are possible without departing from the spirit of the invention as evidenced by the following claims:

What is claimed is:

1. A pressure-sensing compression bandage, comprising:
   a) a plurality of bandage layers;
   b) a plurality of spaced apart pressure sensors disposed on at least one of the bandage layers; the pressure sensors comprising force-sensing resistors including active and receptor areas with associated electrical leads; the active and receptor areas separated by a gap created by a separator such that when pressure is applied by the pressure-sensing compression bandage to a target object, the active and receptor areas contact each other and activate one or more of the pressure sensors to transmit an electrical signal; and
   c) a monitor-controller configured to receive electrical signals from the pressure sensors and adapted to display pressure readings to a user based on the received electrical signals.

2. The pressure-sensing compression bandage of claim 1, wherein the plurality of bandage layers includes an elastic compression layer.

3. The pressure-sensing compression bandage of 2 further comprising a comfort layer and an outer layer and one or more of the comfort layer, outer layer and elastic layer are provided with a medically beneficial substance.

4. The pressure-sensing compression bandage of 3, wherein:
   a) the comfort layer's interior surface is provided with an adhesive disposed as a coating, or in a striped or stippled pattern; or
   b) the outer layer is provided with one or more markings adapted to aid the user in properly wrapping the pressure-sensing compression about the target object; or
   c) the comfort layer's interior surface is provided with a therapeutic insert disposed along an interior side of the comfort layer.

5. The pressure-sensing compression bandage of claim 2; the elastic compression layer comprising elastic layer comprising at least two areas of different elasticities.

6. The pressure-sensing compression bandage of claim 1, wherein the monitor-controller is a portable device that is configured to communicate with the plurality of pressure sensors by direct connection to electrical leads associated therewith or by wireless communication.

7. The pressure-sensing compression bandage of claim 6, wherein the monitor-controller is an appropriately programmed mobile device that communicates with the pressure sensors via a wireless communication protocol.

8. The pressure-sensing compression bandage of claim 1, wherein:
   a) the plurality of pressure sensors are of a type selected from the group consisting of a force-sensitive resistor, a piezoelectric sensor, and a strain gauge; or
   b) the material used to print the force-sensing resistor components and associated electrical leads is an ink material selected from the group consisting of a conductive polymer, a piezoresistive substance, a dielectric material, silver, silver chloride, and carbon.

9. A pressure-sensing compression bandage, comprising:
   a) a plurality of bandage layers, wherein least one of the bandage layers is an elastic layer comprising at least two areas of different elasticities;
   b) a plurality of spaced apart pressure sensors disposed on at least one of the bandage layers other than the elastic layer; the pressure sensors comprising force-sensing resistors including active and receptor areas with associated electrical leads, wherein application of pressure by the pressure-sensing compression bandage to a target object causes the active and receptor areas to contact each other and activate one or more of the pressure sensors to transmit an electrical signal; and
   c) a monitor-controller configured to receive electrical signals from the pressure sensors and adapted to display pressure readings to a user based on the received electrical signals.

10. The pressure-sensing compression bandage of claim 9 further comprising a comfort layer, and an outer layer and one or more of the comfort layer, outer layer and elastic layer are provided with a medically beneficial substance.

11. The pressure-sensing compression bandage of claim 10, wherein the monitor-controller is a portable device that is configured to communicate with the plurality of pressure sensors by direct connection to electrical leads associated therewith or by wireless communication.

12. The pressure-sensing compression bandage of claim 11, wherein the monitor-controller is an appropriately programmed mobile device that communicates with the pressure sensors via a wireless communication protocol.

13. The pressure-sensing compression bandage of claim 11, wherein:
   a) the plurality of pressure sensors are of a type selected from the group consisting of a force-sensitive resistor, a piezoelectric sensor, and a strain gauge; or
   b) the material used to print the force-sensing resistor components and associated electrical leads is an ink material selected from the group consisting of a conductive polymer, a piezoresistive substance, a dielectric material, silver, silver chloride, and carbon.

14. The pressure-sensing compression bandage of 11, wherein:
   a) the comfort layer's interior surface is provided with an adhesive disposed as a coating, or in a striped or stippled pattern; or
   b) the outer layer is provided with one or more markings adapted to aid the user in properly wrapping the pressure-sensing compression bandage about the target object;

c) the comfort layer's interior surface is provided with a therapeutic insert disposed along an interior side of the comfort layer.

\* \* \* \* \*